United States Patent [19]

Chang et al.

[11] Patent Number: 4,663,385
[45] Date of Patent: May 5, 1987

[54] PROCESS FOR THICKENING WITH COPOLYMERS OF ALKYL POLY (OXYALKYLENE) ITACONIC DI-ESTERS

[75] Inventors: Ching-Jen Chang, Chalfont; Travis E. Stevens, Ambler, both of Pa.

[73] Assignee: Rohm and Haas, Philadelphia, Pa.

[21] Appl. No.: 442,341

[22] Filed: Nov. 17, 1982

[51] Int. Cl.$^4$ ............................................. C08L 27/08
[52] U.S. Cl. .................................................... 524/523
[58] Field of Search ......................................... 524/523

[56] References Cited

U.S. PATENT DOCUMENTS

| | | | |
|---|---|---|---|
| 2,798,053 | 7/1957 | Brown | 524/38 |
| 3,708,445 | 1/1973 | Junas et al. | 524/523 |
| 4,075,411 | 2/1978 | Dickstein | 524/43 |
| 4,138,381 | 2/1979 | Chang et al. | 524/765 |
| 4,268,641 | 5/1981 | Koenig et al. | 525/567 |

FOREIGN PATENT DOCUMENTS

| | | |
|---|---|---|
| 0011806 | 6/1980 | European Pat. Off. |
| 0013836 | 8/1980 | European Pat. Off. |

*Primary Examiner*—Paul R. Michl
*Assistant Examiner*—Alex H. Walker
*Attorney, Agent, or Firm*—Douglas E. Winters; Alex R. Sluzas

[57] ABSTRACT

There is disclosed a process of thickening an aqueous system comprising adding to the system aqueous dispersions of water-insoluble emulsion copolymers of (1) about 10–70% by weight of (meth)acrylic acid or itaconic acid, (2) about 0.5–25% by weight of an alkyl poly(oxyethylene) itaconate, and (3) at least 25% by weight, to a total of 100%, of a $C_1$–$C_4$ alkyl (meth)acrylate, and, optionally, included in the total monomer mixture a small amount of (4) about 0.05–1% by weight of a polyethylenically unsaturated monomer. The copolymers, when neutralized and solubilized by addition of an alkali, are high efficiency thickeners for aqueous systems and have improved tolerance to ionic or electrolyte content. Typical systems that can be thickened are paint latices, cosmetic preparations, food preparations, ionic detergents, dye pastes for textiles, pharmaceuticals, and oil well drilling muds. Surfactants enhance the thickening properties afforded by the copolymers.

13 Claims, No Drawings

PROCESS FOR THICKENING WITH COPOLYMERS OF ALKYL POLY (OXYALKYLENE) ITACONIC DI-ESTERS

BACKGROUND OF THE INVENTION

This invention relates to a process of thickening aqueous systems with copolymers, especially emulsion copolymers, to enhancement of such thickening by the addition of surfactants, and to other aspects including coating compositions and other aqueous systems thickened with the polymers.

This application is related to applicant's Ser. No. 101,615, filed Dec. 10, 1979, now abandoned, and corresponding European Patent Publication No. 13,836, dated Aug. 6, 1980, entitled "(Meth)acrylic Acid Emulsion Copolymers for Thickening Purposes". This earlier application discloses emulsion copolymers, and the use thereof as thickeners in aqueous dispersions, of (meth)acrylic acid, and alkyl poly(oxyethylene)(meth)acrylate, and a $C_1-C_4$ alkyl(meth)acrylate, and, optionally, a small amount of a polyethylenically unsaturated monomer.

European Patent Publication No. 11,806, dated June 11, 1980, discloses aqueous emulsion polymers which are pH responsive and are prepared by emulsion polymerization of 15-60% of an $\alpha,\beta$-ethylenically unsaturated carboxylic acid, 15-80% of an $\alpha,\beta$-ethylenically unsaturated monomer, and 1-30% of a nonionic vinyl surfactant ester, preferably a monovinyl ester such as nonylphenoxy poly(ethyleneoxy)9ethyl acrylate.

U.S. Pat. No. 4,138,381 discloses a liquid composition useful as a thickening agent in polymeric latices of (A) 50 weight percent of a polymer of units of (1) 10-98% of an unsaturated $C_3-C_6$ carboxylic acid, (2) about 1-50% of a $C_1-C_{30}$ alkyl(meth)acrylate, and (3) 1-85% of an ester of the formula

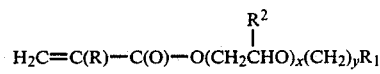

where x is 5-80, y is 0-20, R and $R^2$ are H or $CH_3$, and $R^1$ is alkyl or phenyl; and (B) as a solvent for (A), (4) a glycol, or (5) a glycol containing up to 50% of its weight of water; the composition being made by free radical solution polymerization techniques.

U.S. Pat. No. 4,268,641 discloses a normally solid, base-neutralized copolymer having copolymerized therein about 90-99 mole percent of a carboxy-containing ethylenically unsaturated hydrocarbon and about 1-10 mole percent of a nonionic surfactant acrylate having the formula

wherein R is H or $CH_3$, $R^1$ is a hydrophobe selected from the group consisting of alkyl—O—, alkyl—NH—, and alkyl—CO—, where alkyl contains 4-30 carbon atoms. A is a divalent radical selected from the group consisting of oxyethylene or oxyalkylene units or mixed oxyalkylene units $-(-OC_nH_{2n}-)_x$ where n is an integer from 2 to 4 and x is an integer of 5-40, said surfactant acrylate having an HLB (hydrophilic lipophilic balance) value of about 10-19.

Salts of polyacrylic acid and polymethacrylic acid are well known as thickeners for various aqueous systems. A polyacrylic acid obtained by copolymerizing acrylic acid with a small amount (about 0.2 to 1% by weight on the weight of acrylic acid) of diallyl sucrose (U.S. Pat. No. 2,798,053) has also been sold for use as a thickener for many years. These thickening agents are difficult to handle because they are either powders that are slow to dissolve or very viscous aqueous solutions. Adverse effects such as stiffness or water sensitivity also may be imparted to the finished product by the polymeric acid thickener. Still another problem associated with the acid thickeners is their electrolyte sensitivity. The aqueous systems thickened with these thickeners decrease drastically in viscosity upon addition of an electrolyte, such as sodium chloride.

British Pat. No. 870,994 discloses the preparation of aqueous emulsion copolymers of methacrylic acid and a lower $(C_1-C_4)$alkyl acrylate which gives good thickening upon neutralization. The copolymer dispersions having a solids concentration of 25 to 50% by weight are low viscosity fluids and are thus readily added directly to systems to be thickened. However, they also have severe electrolyte sensitivity.

Japanese Patent Publication No. 31089/1973, published Sept. 26, 1973, discloses a method for the manufacture of aliphatically unsaturated dicarboxylic esters of the formula

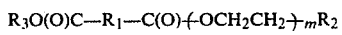

wherein $R_1$ denotes the residue of an aliphatically unsaturated discarboxylic acid, $R_2$ denotes a halogen atom or an organic residue other than a hydroxyl group, $R_3$ denotes an alkyl, aryl, alkylaryl, aralkyl, or alkoxyalkylene glycol residue, and m an integer not less than 5. Homopolymers of these esters and copolymers with other vinyl compounds having an active double bond are disclosed to be useful in the modification of fibers and plastics and as emulsifiers, dispersants, adhesives and "slidants" (sic).

Japanese Patent Publication No. 64216/1975, published May 31, 1975, discloses a method for the manufacture of an aliphatic unsaturated dicarboxylic esters of the formula

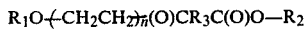

wherein $R_1$ denotes an alkyl group, a phenyl group, or an alkylphenyl group, n an integer not less than 5, $R_3$ denotes a residue of an aliphatic unsaturated dicarboxylic acid and $R_2$ denotes the residue of a lower alcohol. Homopolymers of these esters and copolymers with vinyl compounds having an active double bond are disclosed to be useful in modifying fibers and plastics as emulsifiers, dispersants, adhesives, and "slidants" (sic). The esters of neither Japanese patent publication are disclosed to be useful as thickeners.

The process of this invention is useful for bodying and suspending various mucilaginous and colloidal gel-like systems such as dentrifices, surgical jellies, creams and ointments, printing paste thickeners, and the like. However, most polyelectrolyte solutions decrease drastically in viscosity upon the addition of electrolytes such as sodium chloride. These prior art thickener methods are ion-sensitive and do not adequately maintain the viscosities of water or organic solvent solutions containing inorganic salts such as sodium chloride, even when a third monomer such as 2-ethylhexyl acrylate or styrene, respectively, is included in the polymer as as suggested by the respective prior art patents.

DESCRIPTION OF THE INVENTION

In accordance with the present invention, a process of thickening an aqueous system comprising adding to the system copolymers, especially stable aqueous dispersions of certain water-insoluble emulsions copolymers containing units from an addition polymerizable carboxylic acid, an alkyl poly(oxyalkylene)itaconate and a copolymerizable comonomer, which are quite fluid at a pH below about 7 even though they have solids contents of 25 to 50% or even higher, but upon partial or substantial neutralization with ammonium hydroxide or an alkali metal hydroxide, such as sodium, potassium, or lithium hydroxide, or a volatile amine, such a triethylamine or triethanolamine, because highly viscous and are suitable for thickening aqueous media of a wide variety, using the same general procedure disclosed in the British patent mentioned above. As compared to the thickeners of the British patent, the thickening process of the present invention employs copolymer thickeners containing the polymerized units of alkyl poly(oxyalkylene)itaconates defined herein generally provides markedly greater viscosity at given levels, and has one or more advantages, such as less sensitivity to electrolyte content of the aqueous medium thickened; also improved flow and leveling when used to modify the rheology of latex coating compositions such as water-base paints. In pigment printing pastes for coloring of textiles, the use of the thickening process of the present invention is quite advantageous in respect to use of formulation, compatibility with a wide variety of pigment binders and pigment dispersions, high thickening efficiency resulting in brilliant coloration, good color yield and sharp demarcation, freedom from flushing and haloing, minimal stiffening of the printed area, resistance to crocking, to washing, to drycleaning, and to exposure to sunlight. In "all-aqueous" silk screen pigment printing systems, the process of thickening of the present invention provides convenience of handling, good color depth, sharp mark detail with no haloing, and improved "holdout", i.e. less "strikethrough".

This invention comprises a process of thickening an aqueous system, comprising adding to the system a copolymer obtained by copolymerization of a monomer system comprising (1) at least about 10 weight percent of a copolymerizable ethylenically unsaturated monomer or monomer mixture selected from the group consisting of methacrylic acid, acrylic acid, itaconic acid, acryloxypropionic acid, maleic acid, fumaric acid, citraconic acid and crotonic acid; and (2) about 0.5 to 30 weight percent of at least one monomer of the formula

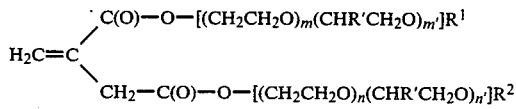

wherein $R^1$ and $R^2$, independently, are selected from the group consisting of hydrogen and alkyl, alkylaryl and polycyclic alkyl groups having 1 to 30 carbon atoms;

m, m', n and n', independently, are zero or a number having an average value of up to 60 or more, provided that at least one of m and n is at least 2 and provided that the $R^1$ or $R^2$ group, when m or n, respectively, is at least 2, is one of said alkyl, alkylaryl and polycyclic alkyl groups having at least 8 carbon atoms;

R' is $C_1$-$C_2$ alkyl; and the expressions $[(CH_2CH_2O)_m(CHR'CH_2O)_{m'}]R^1$ and $[(CH_2CH_2O)_n(CHR'CH_2O)_{n'}]R^2$ means that the groups $(CH_2CH_2O)_m$ and $(CHR'CH_2O)_{m'}$ and the groups $(CH_2CH_2O)_n$ and $(CHR'CH_2O)_{n'}$, respectively, may be present in any random order or may be present in the exact order $(CH_2CH_2O)_m(CHR'CH_2O)_{m'}R^1$ or $(CH_2CH_2O)_n(CHR'CH_2O)_{n'}R^2$; and (3) optionally at least one compound of the formula $$H_2C=CYZ$$

wherein (a) Y is H and Z is COOR'', $C_6H_4R'''$, CN, Cl, OC(O)R'''', $CONH_2$, or $CH=CH_2$;

(b) Y is $C_1$-$C_4$ alkyl and Z is COOR'', $C_6H_4R'''$, CN, $CONH_2$, or $CH=CH_2$; or (c) Y and Z are Cl; and R'' is $C_1$-$C_8$ alkyl or $C_2$-$C_8$ hydroxyalkyl or lower alkoxy($C_2$-$C_8$)alkyl; R''' is H, Cl, Br or $C_1$-$C_4$ alkyl; and R'''' is $C_1$-$C_8$ alkyl; and (4) zero to 1.0 weight percent of a polyethylenically unsaturated monomer.

Component (1) is preferably a polymerizable, monoethylenically unsaturated carboxylic acid selected from methacrylic acid, acrylic acid, itaconic acid and acryloxypropionic acid. More preferably, this component is methacrylic acid.

Component (3) is preferably a $C_1$-$C_4$ alkyl(meth)acrylate, more preferably ethyl acrylate, butyl acrylate, or methyl methacrylate; most preferably ethyl acrylate.

Preferably, this invention comprises a process of thickening an aqueous system, comprising adding to the system an aqueous dispersion of a water-insoluble emulsion copolymer obtained by aqueous emulsion copolymerization of a monomer system comprising (1) about 10 to 70 weight percent of at least one member selected from the group consisting of methacrylic acid, acrylic acid, acryloxypropionic acid, and itaconic acid;

(2) about 0.5 to 25 weight percent of at least one monomer of the formula

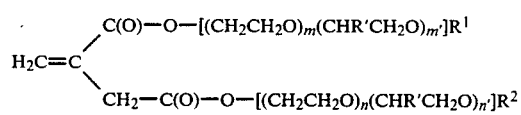

wherein $R^1$ and $R^2$, independently, are selected from the group consisting of hydrogen and alkyl, alkylaryl and polycyclic alkyl groups having 1 to 30 carbon atoms;

m, m', n and n', independently, are zero or a number having an average value of up to 60 or more, provided that at least one of m and n is at least 2 and provided that the $R^1$ or $R^2$ group, when m or n, respectively, is at least 2, is one of said alkyl, alkylaryl and polycyclic alkyl groups having at least 8 carbon atoms;

R' is $C_1$-$C_2$ alkyl; and the expressions $[(CH_2CH_2O)_m(CHR'CH_2O)_{m'}]R^1$ and $[(CH_2CH_2O)_n(CHR'CH_2O)_{n'}]R^2$ mean that the groups $(CH_2CH_2O)_m$ and $(CHR'CH_2O)_{m'}$, and $(CH_2CH_2O)_n$ and $(CHR'CH_2O)_{n'}$, respectively, may be present in any random order or may be present in the exact order $(CH_2CH_2O)_m(CHR'CH_2O)_{m'}R^1$ or $(CH_2CH_2O)_n(CHR'CH_2O)_{n'}R^2$;

(3) at least 25 weight percent of a copolymerizable ethylenically unsaturated monomer or a monomer mixture selected from the group consisting of compounds of the formula $$H_2C=CYZ$$

wherein
(a) Y is H and Z is COOR'', $C_6H_4R'''$, CN, Cl, OC(O)R'''', $CONH_2$ or $CH=CH_2$;
(b) Y is $C_1$-$C_4$ alkyl and Z is COOR'', $C_6H_4R'''$, $CONH_2$, CN or $CH=CH_2$; or
(c) Y and Z are Cl; and R'' is $C_1$-$C_8$ alkyl or $C_2$-$C_8$ hydroxyalkyl or lower alkoxy($C_2$-$C_8$)alkyl; R''' is H, Cl, Br or $C_1$-$C_4$ alkyl; and R'''' is $C_1$-$C_8$ alkyl; and
(4) zero to 1.0 weight percent of a polyethylenically unsaturated monomer;
the total of the percentages of monomers (1), (2), (3), and (4) being 100.

More preferably, this invention comprises a process of thickening an aqueous system, comprising adding to the system an aqueous dispersion of a water-insoluble emulsion copolymer obtained by aqueous emulsion copolymerization of a monomer system comprising
(1) about 10 to 70 weight percent of at least one of acrylic acid, methacrylic acid, acryloxypropionic and itaconic acid;
(2) about 0.5 to 25 weight percent of at least one mono- or di-ester of itaconic acid wherein at least one of the two itaconic acid carboxy groups is esterified by a $C_8$-$C_{30}$ hydrocarbyl poly(oxyalkylene) group, the poly(oxyalkylene) moiety being at least two $C_2$-$C_4$ oxyalkylene groups; and
(3) at least 25 weight percent of at least one copolymerizable ethylenically unsaturated comonomer selected from $C_1$-$C_8$ alkyl, $C_2$-$C_8$ hydroxyalkyl and lower alkoxy($C_2$-$C_8$)alkyl acrylates, methacrylates, and 1-alkenoates containing four to six carbons in the alkene-carbon chain; styrene and vinyl[($C_1$-$C_8$)alkyl]benzene, and [($C_1$-$C_8$)alkylphenoxy]alkenes containing three to six carbons in the alkene-carbon chain; acrylonitrile, methacrylonitrile, and cyanoalkenes containing four to six carbons in the alkene-carbon chain; vinyl and vinylidene chloride; vinyl esters of $C_2$-$C_9$ saturated aliphatic carboxylic acids; and polyethylenically unsaturated monomers
and by at least partially neutralizing said copolymer.

In a more preferred embodiment, this invention comprises a process of thickening an aqueous system comprising adding to the system a copolymer, and dispersions thereof, obtainable by aqueous emulsion copolymerization of a monomer system comprising:
(1) about 10 to 70 weight percent of at least one member selected from the group consisting of methacrylic acid, acrylic acid, acryloxypropionic acid and itaconic acid;
(2) about 0.5 to 25 weight percent of at least one monomer of the formula

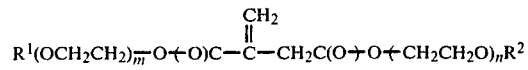

wherein
$R^1$ and $R^2$, independently, are selected from the group consisting of hydrogen and alkyl, alkylaryl and polycyclic alkyl groups having 1 to 30 carbon atoms; and
m and n, independently, are zero or a number having an average value of up to 60 or more, provided that at least one of the $R^1$ or $R^2$ groups, when m or n, respectively, is at least 2, is one of said alkyl, alkylaryl, and polycyclic alkyl groups having at least 8 carbon atoms (3) at least 25 weight percent of at least one alkyl(meth)acrylate in which the alkyl group has 1 to 4 carbon atoms; and
(4) zero to 1.0 weight percent of a polyethylenically unsaturated monomer;
the total of the percentages of monomers (1), (2), (3) and (4) being 100.

Preferably this process is accomplished using a water-insoluble emulsion copolymer obtained by aqueous emulsion copolymerization of a monomer system consisting essentially of about 30 to 45 weight percent of component (1) above, about 1 to 15 weight percent of component (2) above, and about 40 to 60 weight percent of component (3) above.

Preferably this process is effected using a water-insoluble emulsion copolymer which is a mono- or di-ester of itaconic acid wherein at least one of the two itaconic acid carboxy groups is esterified by a $C_8$-$C_{30}$ hydrocarbyl poly(oxyethylene) group, the poly(oxyethylene) moiety being at least two oxyethylene groups.

More preferably this process is accomplished using a water insoluble emulsion polymer wherein component (2) above is a di-ester of itaconic acid wherein the two itaconic acid carboxy groups are each esterified by a $C_{12}$-$C_{18}$ hydrocarbyl poly(oxyethylene) group, the poly(oxyethylene) moiety being at least two oxyethylene groups.

In addition it is preferred that component (3) above of the water-insoluble emulsion copolymer is at least one of $C_1$-$C_4$ alkyl acrylates and methacrylates.

Still more preferably this process is carried out using a water-insoluble emulsion copolymer obtained by aqueous emulsion copolymerization of a monomer system comprising:
(1) about 30 to 45 weight percent of methacrylic acid;
(2) about 1 to 15 weight percent of di-ester of itaconic acid wherein the two itaconic acid carboxy groups are each esterified by a $C_{12}$-$C_{18}$ hydrocarbyl poly(oxyethylene) group, the average value of the number of oxyethylene groups in each poly(oxyethylene) chain being at least 10; and
(3) about 40 to 60 weight percent of ethyl acrylate.

The alkyl poly(oxyalkylene)itaconates employed in this invention are compounds of the formula

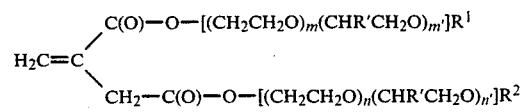

wherein
R¹ and R², independently, are selected from the group consisting of hydrogen and alkyl, alkylaryl and polycyclic alkyl groups having 1 to 30 carbon atoms;

m, m', n and n', independently, are zero or a number having an average value of up to 60 or more, provided that at least one of m and n is at least 2 and provided that the R¹ or R² group, when m or n, respectively, is at least 2, is one of said alkyl, alkylaryl and polycyclic alkyl groups having at least 8 carbon atoms;

R' is $C_1$–$C_2$ alkyl; and the expressions [(CH$_2$CH$_2$O)$_m$(CHR'CH$_2$O)$_{m'}$]R¹ and [(CH$_2$CH$_2$O)$_n$(CHR'CH$_2$O)$_{n'}$]R² mean that the groups (CH$_2$CH$_2$O)$_m$ and (CHR'CH$_2$O)$_{m'}$ and the groups (CH$_2$CH$_2$O)$_n$ and (CHR'CH$_2$O)$_{n'}$, respectively, may be present in any random order or may be present in the exact order (CH$_2$CH$_2$O)$_m$(CHR'CH$_2$O)$_{m'}$R¹ or (CH$_2$CH$_2$O)$_n$(CHR'CH$_2$O)$_{n'}$R².

Preferably, the alkyl poly(oxyalkylene)itaconates employed in the invention are compounds of the formula

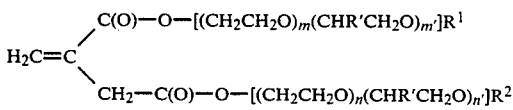

wherein
R¹ and R², independently, are selected from the group consisting of hydrogen and alkyl, alkylaryl and polycyclic alkyl groups having 1 to 30 carbon atoms;

m and n, independently, are zero or a number having an average value of up to 60 or more, provided that at least one of m and n is at least 2 and provided that at least one of the R¹ or R² groups, when m or n, respectively, is at least 2, is one of said alkyl, alkylaryl, and polycyclic alkyl group having at least 8 carbon atoms;

The novel and improved copolymers according to the present invention are obtainable by copolymerization of a monomer system comprising:

(1) about 0.5 to 30 weight percent of at least one monomer of the formula

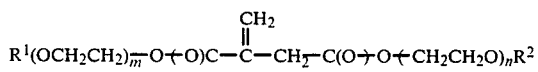

wherein
R¹ and R², independently, are selected from the group consisting of hydrogen and alkyl, alkylaryl and polycyclic alkyl groups having 1 to 30 carbon atoms;

m, m', n and n', independently, are zero or a number having an average value of up to 60 or more, provided that at least one of m and n is at least 2 and provided that the R¹ or R² group, when m or n, respectively, is at least 2, is one of said alkyl, alkylaryl and polycyclic alkyl groups having at least 8 carbon atoms;

R' is $C_1$–$C_2$ alkyl; and the expressions [(CH$_2$CH$_2$O)$_m$(CHR'CH$_2$O)$_{m'}$]R¹ and [(CH$_2$CH$_2$O)$_n$(CHR'CH$_2$O)$_{n'}$]R² means that the groups (CH$_2$CH$_2$O)$_m$ and (CHR'CH$_2$O)$_{m'}$ and the groups (CH$_2$CH$_2$O)$_n$ and (CHR'CH$_2$O)$_{n'}$, respectively, may be present in any random order or may be present in the exact order (CH$_2$CH$_2$O)$_m$(CHR'CH$_2$O)$_{m'}$R¹ or (CH$_2$CH$_2$O)$_n$(CHR'CH$_2$O)$_{n'}$R²; and (2) at least about 10 weight percent of at least one copolymerizable ethylenically unsaturated monomer selected from the group consisting of methacrylic acid, acrylic acid, itaconic acid, acryloxypropionic acid, maleic acid, fumaric acid, citraconic acid and crotonic acid; and (3) optionally at least one compound of the formula $$H_2C=CYZ$$

wherein
(a) Y is H and Z is COOR'', C$_6$H$_4$R''', CN, Cl, OC(O)R'''', CONH$_2$, or CH=CH$_2$;

(b) Y is $C_1$–$C_4$ alkyl and Z is COOR'', C$_6$H$_4$R''', CONH$_2$, CN or CH=CH$_2$; or (c) Y and Z are Cl; and R'' is $C_1$–$C_8$ alkyl or $C_2$–$C_8$ hydroxyalkyl or lower alkoxy($C_2$–$C_8$)alkyl; R''' is H, Cl, Br or $C_1$–$C_4$ alkyl; and R'''' is $C_1$–$C_8$ alkyl; and (4) zero to 1.0 weight percent of a polyethylenically unsaturated monomer.

The copolymer can be an emulsion copolymer obtainable by copolymerization of the monomers in an aqueous or inverse emulsion system, a suspension copolymer, a precipitation copolymer, a solution copolymer, a normally solid copolymer or a non-aqueous dispersion (NAD) copolymer.

In a preferred embodiment, the copolymer, and dispersions thereof, employed by the present invention are those obtainable by aqueous emulsion copolymerization of a monomer system comprising:

(1) about 10 to 70 weight percent of at least one member selected from the group consisting of methacrylic acid, acrylic acid, acryloxypropionic acid and itaconic acid;

(2) about 0.5 to 25 weight percent of at least one monomer of the formula

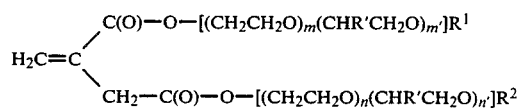

wherein
R¹ and R², independently, are selected from the group consisting of hydrogen and alkyl, alkylaryl and polycyclic alkyl groups having 1 to 30 carbon atoms;

m, m', n and n', independently, are zero or a number having an average value of up to 60 or more, provided that at least one of m and n is at least 2 and provided that the R¹ or R² group, when m or n, respectively, is at least 2, is one of said alkyl, alkylaryl and polycyclic alkyl groups having at least 8 carbon atoms;

R' is $C_1$–$C_2$ alkyl; and the expressions [(CH$_2$CH$_2$O)$_m$(CHR'CH$_2$O)$_{m'}$]R¹ and [(CH$_2$CH$_2$O)$_n$(CHR'CH$_2$O)$_{n'}$]R² mean that the groups (CH$_2$CH$_2$O)$_m$ and (CHR'CH$_2$O)$_{m'}$ and the groups (CH$_2$CH$_2$O)$_n$ and (CHR'CH$_2$O)$_{n'}$, respectively, may be present in any random order or may be present in the exact order (CH$_2$CH$_2$O)$_m$(CHR'CH$_2$O)$_{m'}$R¹ or (CH$_2$CH$_2$O)$_n$(CHR'CH$_2$O)$_{n'}$R²;

(3) at least 25 weight percent of at least one copolymerizable ethylenically unsaturated monomer selected from the group consisting of a compound of the formula $$H_2C=CYZ$$

wherein
(a) Y is H and z is COOR'', $C_6H_4R'''$, CN, Cl, OC(O)R'''', $CONH_2$ or $CH=CH_2$;
(b) Y is $C_1-C_4$ alkyl and Z is COOR'', $C_6H_4R'''$, $CONH_2$, CN or $CH=CH_2$; or
(c) Y and Z are Cl; and R'' is $C_1-C_8$ alkyl or $C_2-C_8$ hydroxyalkyl or lower alkoxy($C_2-C_8$)alkyl; R''' is H, Cl, Br or $C_1-C_4$ alkyl; and R'''' is $C_1-C_8$ alkyl; and
(4) zero to 1.0 weight percent of a polyethylenically unsaturated monomer;
the total of the percentages of monomers (1), (2), (3), and (4) being 100.

In a more preferred embodiment, the copolymers, and dispersions thereof, employed by the present invention are those obtainable by aqueous emulsion copolymerization of a monomer system comprising
(1) about 10 to 70 weight percent of at least one member selected from the group consisting of methacrylic acid, acrylic acid, acryloxypropionic acid and itaconic acid;
(2) about 0.5 to 25 weight percent of at least one monomer of the formula

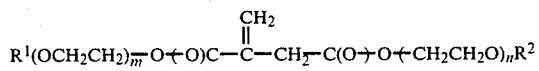

wherein
$R^1$ and $R^2$, independently, are selected from the group consisting of hydrogen and alkyl, alkylaryl and polycyclic alkyl groups having 1 to 30 carbons atoms; and
m and n, independently, are zero or a number having an average value of up to 60 or more, provided that at least one of m and n is at least 2 and provided that at least one of the $R^1$ or $R^2$ groups, when m or n, respectively, is at least 2, is one of said alkyl, alkylaryl, and polycyclic alkyl groups having at least 8 carbon atoms;
(3) at least 25 weight percent of at least one copolymerizable ethylenically unsaturated monomer selected from the group consisting of a compound of the formula $$H_2C=CYS$$

wherein
(a) Y is H and z is COOR'', $C_6H_4R'''$, CN, Cl, OC(O)R'''', $CONH_2$ or $CH=CH_2$;
(b) Y is $C_1-C_4$ alkyl and Z is COOR'', $C_6H_4R'''$, CN, $CONH_2$, or $CH=CH_2$; or
(c) Y and Z are Cl.

More preferably, component (3) in the emulsion copolymer is a $C_1-C_4$ alkyl (meth)acrylate, preferably ethyl acrylate, butyl acrylate or methyl methacrylate, most preferably ethyl acrylate.

In an especially prefered embodiment, the invention employs a water-insoluble emulsion copolymer having the composition:
(1) about 30 to 45 weight percent of methacrylic acid;
(2) about 1 to 15 weight percent of at least one monomer of the formula:

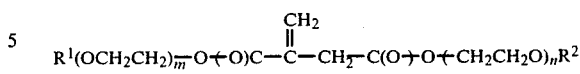

wherein
$R^1$ and $R^2$, independently, are alkyl groups having 12 to 18 carbon atoms and m and n, independently, have an average value of about 10 to 60; and
(3) about 40 to 60 weight percent of ethyl acrylate.

The emulsion copolymers employed in the present invention may be produced by conventional aqueous emulsion polymerization techniques, using appropriate emulsifiers for emulsifying the monomer and for maintaining the polymer obtained in a stable, dispersed condition. Commonly used anionic surfactants such as sodium lauryl sulfate, dodecylbenzene sulfonate and ethoxylated fatty alcohol sulfate can be used as emulsifiers. The emulsifier may be used in a proportion of ½ to 6% of the weight of monomers.

Preferably, water-soluble initiators such as alkali metal or ammonium persulfate are used in amounts from 0.01 to 1.0% on the weight of monomers. A gradual addition thermal process employed at temperatures between 60° C. to 100° C. is preferred over redox systems.

The polymerization system may contain small amounts (0.01 to 5% by weight, based on monomer weight) of the chain transfer agent mercaptans such as hydroxyethyl mercaptan, β-mercaptopropionic acid and alkyl mercaptans containing from about 4 to 22 carbon atoms. The use of mercaptan modifier reduces the molecular weight of the polymer and therefore its thickening efficiency. This may be desirable in certain areas of applications where proper rheology but not the thickening efficiency is of primary concern.

The copolymers hereinabove defined may further be modified by introducing a small amount of component (4), namely, a polyethylenically unsaturated copolymerizable monomer effective for crosslinking, such as diallylphthalate, divinylbenzene, allyl methacrylate, or ethyleneglycol dimethacrylate. Thus, from 0.05 to 1.0% of such polyethylenically unsaturated compound based on total weight of monomer may be included in the composition forming the polymer. The resulting copolymers are eigher highly branched or in the form of three-dimensional networks. In the neutralized salt form, those networks swell in an aqueous system and the consequent "micro-gel" structure acts as a highly efficient thickener.

The copolymer may be utilized in a variety of ways to provide the thickener or thickened compositions of the invention. For example, the copolymer, while in aqueous dispersion or dry form, may be blended into an aqueous system to be thickened followed by addition of a neutralizing agent. Alternatively, the copolymer may first be neutralized in aqueous dispersion form and then blended with the aqueous system. Preferably, if cothickening by a surfactant is desired, the components are separately blended (as dry components or as dispersions or slurries) into an aqueous dispersion to be thickened, followed by the neutralization step. Although aqueous concentrates of the copolymer in acid form and the surfactant may be formed and added to an aqueous dispersion to be thickened as needed, followed by neutralization, such concentrates tend to be too viscous for easy handling. It is nevertheless possible to prepare either a dry blend or an aqueous, high solids composition which is sufficiently low in viscosity as to be pumpable or pourable, and then to further thicken the admixture by addition of an alkaline material.

The copolymer thickener may be provided in a dry state in a number of ways. For example, the unneutralized copolymer may be spray or drum dried and, if desired, blended with a surfactant cothickener. However, it is also possible to spray dry or otherwise dehydrate the neutralized copolymer thickener, and then reconstitute the aqueous thickener dispersion at a future time and place by agitation in an aqueous medium, provided the pH of the dispersion is maintained at pH 7 or higher.

The more usual method of application of the dispersion employed in the present invention for aqueous thickening is to add the aqueous dispersion of the carboxylic acid copolymer to the medium to be thickened and, after mixing, to introduce an alkaline material to neutralize the acid. The major portion of the thickening effect is obtained in a few minutes upon neutralization. In the presence of high concentrations of electrolytes, the viscosity development may take much longer. This method of applying a copolymer emulsion to an aqueous system before neutralization enables one to handle a high solids thickener in a non-viscous state, to obtain a uniform blend, and then to convert to a highly viscous condition by the simple addition of an alkaline material to bring the pH of the system to 7 or above.

The aqueous solutions thickened with the neutralized latex copolymer employed in this invention exhibit good viscosity stability even at pH as high as 13.

The copolymer may be used to thicken compositions under acidic conditions in the presence of a relatively large amount of surfactant wherein the thickened composition, for example, an aqueous system, has a pH below 7, even as low as 1.

The process of thickening described here is useful in a variety of aqueous systems, such as textile printing pastes, latex paint formulations, cosmetic formulations, pigment dispersions, oil well drilling fluids, dentrifices, hand lotions, and liquid detergents.

SURFACTANT COTHICKENING

A remarkable enhancement of thickening (herein termed "cothickening") has been observed upon the addition of a surfactant to an aqueous system containing emulsion copolymer employed in the invention, when the emulsion copolymer is neutralized. In some cases the thickening can be enhanced up to about 40 times the viscosity afforded by the neutralized copolymer alone. A wide range of surfactant type and amount is effective. Generally, the surfactant may be used in an amount of about 0.1 to 0.5 parts surfactant per part copolymer, same basis. Although trace amounts of surfactant may be residually present from the emulsion polymerization of the monomers comprising the emulsion copolymer (for example, whatever may remain of the about 1.5 weight percent surfactant on monomers), such amounts of surfactant are not believed to result in any measurable cothickening.

On the basis of an aqueous system containing about 0.1 to 5% by weight of copolymer solids, a useful amount of surfactant for optimum cothickening is about 0.01 to 1.0% by weight of the total system. As indicated, the amounts of copolymer and surfactant cothickener may vary widely, even outside these ranges, depending on copolymer and surfactant type and other components of the aqueous system to be thickened. However, it has been observed that the cothickening reaches a maximum as surfactant is added and then decreases. Hence, it may be uneconomical to employ surfactant in amounts outside the stated concentrations and copolymer/surfactant ratios, but this can be determined in a routine manner in each case.

This invention also comprises the process of thickening an aqueous system comprising the addition of an aqueous dispersion of a water-insoluble emulsion copolymer and a surfactant said surfactant being present in an amount effective to thicken the dispersion beyond the thickening provided by at least partial neutralization of said emulsion copolymer. Preferably the surfactant employed in this process is anionic or nonionic.

The preferred method of application of the emulsion copolymer and the surfactant for aqueous thickening is to add in any sequence the copolymer and the surfactant to the medium to be thickened and, after mixing, to introduce an alkaline material to neutralize the acid. This method of applying copolymer emulsion and surfactant to an aqueous system before neutralization enables one to handle a high solids thickener in a non-viscous state, to obtain a uniform blend, and then to convert to a highly viscous condition by the simple addition of an alkaline material to bring the pH of the system to 7 or above. However, the copolymer in the aqueous system may also be neutralized before addition of the surfactant.

The surfactants which may be used include nonionics and anionics, singly or in combination, the selection necessarily depending upon compatibility with other ingredients of the thickened or thickenable dispersions of the invention. Cationic and amphoteric surfactants may also be used provided they are compatible with the copolymer and other ingredients of the aqueous system, or are used in such small amounts as not to cause incompatibility.

Suitable anionic surfactants that may be used include the higher fatty alcohol sulfates such as the sodium or potassium salt of the sulfates of alcohols having from 8 to 18 carbon atoms, alkali metal salts or amine salts of high fatty acid having 8 to 18 carbon atoms, and sulfonated alkyl aryl compounds such as sodium dodecyl benzene sulfonate. Examples of nonionic surfactants include alkylphenoxypolyethoxyethanols having alkyl groups of about 7 to 18 carbon atoms and about 9 to 40 or more oxyethylene units such as octylphenoxypolyethoxyethanols, dodecylphenoxypolyethoxyethanols; ethylene oxide derivatives of long-chain carboxylic acids, such as lauric, myristic, palmitic, oleic; ethylene oxide condensates of long-chain alcohols such as lauryl or cetyl alcohol, and the like.

Examples of cationic surfactants include lauryl pyridinium chloride, octylbenzyltrimethylammonium chloride, dodecyltrimethylammonium chloride, condensates of primary fatty amines and ethylene oxide, and the like.

The foregoing and numerous other useful nonionic, anionic, cationic, and amphoteric surfactants are described in the literature, such as "McCutcheon's Detergents & Emulsifiers 1978 Annual, North America Edition", MC Publishing Company, Glen Rock, NJ 07452, U.S.A., incorporated herein by reference.

A water-in-oil clear concentrate may be prepared, for example, by dissolving 5 parts of a surfactant, such as sorbitan mono-oleate, in 30 parts by weight of mineral spirits (a hydrocarbon distillate cut having a flash point over 102° C.), then adding while stirring 58 parts of one of the emulsion polymers of the present invention, e.g., one of the copolymers in Table II below, at 30% solids and mixing therein 7 parts of 28% ammonium hydroxide to at least partially neutralize the polymer dispersion and thereby thicken it. The resulting composition may be useful as a clear concentrate that can be diluted with about 95 to 98 parts of water to form a printing clear. Such a clear can then be mixed with an aqueous emulsion polymer to serve as a binder, and, if desired, with a color concentrate. The commercial practice to date has been to prepare water-in-oil types of clear concentrates commonly used for the textile printing and dyeing industry by mixing a dusty, powdered thickener, such as certain dry products of U.S. Pat. No. 2,798,053 with the other ingredients. The use of polycarboxylic acid thickeners in the form of aqueous emulsion polymer dispersions for preparation of printing compositions for the textile printing and dyeing industry, though suggested in the British patent (page 6, lines 58 to 70), has not been accepted commercially, presumably becaue of inadequate thickening efficiency obtained by the use of such emulsion polymer dispersions and/or the lack of reliable viscosity expectations in the event of adventitious presence of cations, such as sodium, calcium, magnesium, which may be present in hard water used or in the case of sodium, present in a softened water in an amount that varies in dependence upon unreliable deionization. The possibility of adventitious occurrence of such cations, espcially that of sodium, is particularly rampant in the commercially available pigment or color concentrates. The emulsion copolymers of the present invention are expected to provide a more efficient thickening effect and are less sensitive to the presence, adventitiously or otherwise, of such cations.

This invention also comprises the process of thickening textile printing composition comprising a water-in-oil clear concentrate containing a surfactant, such as sortitan mono-oleate, dissolved in a hydrocarbon distillate, such as mineral spirits having a flash point over 120° C., and an aqueous dispersion of an emulsion copolymer of (meth)acrylic acid mixed therewith to emulsify the water thereof in the hydrocarbon solution, the copolymer being then thickened by at least partial neutralization by a base, such as ammonium hydroxide, the resulting concentrate being dilutable with water to form a printing clear which can be mixed with an aqueous vinyl addition emulsion polymer to serve as a binder, and optionally with a color concentrate to form a pigment paste for pigment printing, and dyeing of textiles.

Preferably the process comprises a textile printing composition comprising a water-in-oil clear concentrate, additional water, an aqueous dispersion of a binder comprising a vinyl addition emulsion polymer having a heat-reactive component therein, and a color concentrate, the several components being mixed to form a pigment paste having desired rheological properties suitable for the pigment printing and dyeing of textiles.

Pigment pastes may be prepared using various color concentrates from the printing clear obtained as described in the foregoing paragraph by the addition of a color concentrate, e.g., Aqua Hue Blue BGG 9521, and an aqueous emulsion copolymer binder in accordance with the following print paste code or chart:

| Print Paste Code | A | B | C | D |
|---|---|---|---|---|
| Printing clear | 80 | 80 | 80 | 80 |
| Binder (35% Solids) | 10 | 10 | 10 | 10 |
| Color Concentrate | — | 0.6 | 3 | 10 |

The following commercially available colorants may be used in place of the Aqua Hue Blue BGG 9521, each of the following being used to produce printing pastes having color levels corresponding to B, C, and D:
1. Magenta W-5030
2. Aqua Hue Scarlet BYDC
3. Helizarine Red BN
4. Blue 3G Type W
5. Blue 2G This invention also comprises the process of thickening a dentrifice using at least one of the copolymers disclosed above. For example, a dentrifice may be prepared using one of the polymers of Table II by mixing 1.7 parts of a 30% solids dispersion of the copolymer into a mixture of 20 parts sorbitol and 1.5 parts of sodium lauryl sulfate. Then 0.07 part of sodium hydroxide is mixed in thoroughly to thicken the mixture to 50 parts of finely-divided calcium carbonate is mixed in water (about 27 parts) being mixed in gradually to form a uniform paste.

This invention also comprises the process of thickening a hand lotion using at least one of the copolymers disclosed above. For example, a hand lotion may be prepared by mixing 48.5 parts of glycerine with 1.7 parts of a 30% solids dispersion of one of the copolymers of Table II, adding 0.5 part triethanolamine while stirring and adding about 50.5 parts of water gradually to form an unctuous liquid.

This invention also comprises the process of thickening a liquid detergent using at least one of the copolymers disclosed above. For example, an all-purpose liquid detergent for household use may be made by mixing the following ingredients in the proportions (parts) and in the order specified in the table:

| | |
|---|---|
| Tetrapotassium pyrophosphate | 1.0 |
| 2-Butoxyethanol | 2.0 |
| TRITON ® X-100 [octylphenoxy (ethyleneoxy) $_{9-10}$ ethanol] | 1.0 |
| Copolymer of Table II (30% solids) | 1.3 |
| NaOH | 0.2 |
| Water | 94.5 |

This invention also comprises the process of thickening an oil well drilling fluid using at least one of the copolymers disclosed above. For example, a "fracturing" fluid for stimulating the production of oil from oil-wells may simply be made up by mixing one part of a 25% to 30% solids dispersion of one of the polymers of the invention listed in Table II with about 0.04 part of NaOH and sufficient water to make a total of 100 parts.

This invention also comprises the process of thickening a pigment paste using at least one of the copolymers disclosed above. For example, a pigment dispersion for use in making a water-base paint employing aqueous emulsion vinyl addition polymers, e.g. of acrylic esters, vinyl acetate, styrene-butadiene, etc. as the primary binder, may be prepared by mixing a pigment, such as $TiO_2$, with a pigment dispersant, e.g. Tamol ® 731 or Tamol 850, with a copolymer dispersion of the present invention listed in Table II with water and neutralizing with a basic material, e.g. NH$_3$, NaOH, or triethylamine. A suitable formulation is the following, the parts of pigment, dispersant and thickening copolymer of the invention listed in Table II being based on solids.

| Ingredient | Parts |
|---|---|
| Pigment | 60.0 |
| Dispersant | 0.18 |
| Polymer (e.g. 30% solids) | 0.4 |
| NaOH | 0.06 |
| Water (to make 100) | -balance |

This invention also comprises the process of using at least of the copolymer emulsions disclosed above to thicken a water-base paint comprising an aqueous dispersion of a vinyl addition emulsion polymer binder selected from vinyl acetate polymers, polymers of esters of acrylic acid, polymers of esters of methacrylic acid, and styrene-butadiene polymers, copolymers of vinyl acetate and esters of acrylic acid, copolymers of vinyl acetate and esters of methacrylic acid, copolymers of vinyl acetate and esters of acrylic and methacrylic acid and copolymers of esters of acrylic and methacrylic acid, said paint containing a pigment having a PVC up to 65%, and containing at least partially neutralized emulsion copolymers to control the rheological properties of the paint.

In the following examples illustrative of the invention, the parts and percentages are by weight and the temperatures are in Celsius degrees unless otherwise stated.

The following Example A is a suitable procedure for producing the itaconate ester of the invention, which ester also constitutes component (2) of the emulsion copolymer of the invention.

EXAMPLE A

Preparation of Alkyl Poly(oxyethylene) Itaconate Ester Monomer

A 1 liter four-necked flask fitted with a mechanical stirrer, thermometer, air ebullator and distillation head (with automatic isothermal distillation control) atop a 9 plate, vacuum jacketed, Oldershaw column was charged with 454 g (0.4 moles) stearyloxy poly(ethyleneoxy)$_{19}$ ethanol, 300 g toluene and 0.016 g p-methoxyphenol (1.3×10$^{-4}$ mole). The mixture was heated at reflux to remove residual water by azeotropic distillation. The resulting solution was cooled to 85° C. and 31.6 g of dimethyl itaconate (0.2 moles) was added followed by 5.3 g of tetraisopropyl titanate. The solution was heated again to reflux. The head temperature initially rose to 108° C. and then slowly fell to 64.5° C. as methanol was generated. The automatic distillation head was set so that 100% of the distillate was collected below 65° C. After two hours, the automatic distillation head was adjusted to collect 50% of the distillate up to 100° C. Two hours thereafter, methanol was no longer observed in the distillate (GLC), and the reaction was terminated. The total distillate obtained was 45 g (28.5% methanol, 100% of theory). The mixture was vacuum stripped to remove toluene to give a waxy solid product distearyl poly(oxyethylene)$_{20}$ itaconate, which is monomer #6 in Table I.

In the following Table I, there are listed several representative alkyl poly(oxyethylene)itaconate ester monomers produced according to Example A used to make the emulsion copolymer thickeners.

TABLE I

Alkyl Poly(oxyethylene) Itaconates $$R^1(OCH_2CH_2)_{\overline{m}}O(O)C-\underset{\underset{CH_2}{\|}}{C}-CH_2-C(O)O(CH_2CH_2O)_nR^2$$

| Monomer No. | R$^1$ | R$^2$ | m | n |
|---|---|---|---|---|
| 1 | H | lauryl | 0 | 23 |
| 2 | methyl | lauryl | 0 | 23 |
| 3 | lauryl | lauryl | 23 | 23 |
| 4 | H | stearyl | 0 | 20 |
| 5 | methyl | stearyl | 0 | 20 |
| 6 | stearyl | stearyl | 20 | 20 |

The following Example B illustrates a suitable procedure for producing the water-insoluble emulsion copolymers of the invention.

EXAMPLE B

Preparation of Emulsion Copolymer Thickener Dispersion Containing Units of Alkyl Poly(oxyethylene) Itaconate Ester Monomer An emulsion of monomers in water was prepared by mixing 118 g of ethyl acrylate, 94.4 g of methacrylic acid, 23.6 g of monomer prepared in Example A, 6.3 g of 28% sodium lauryl sulfate, and 271 g of water. To a reaction vessel containing 6.3 g of sodium lauryl sulfate in 206 g of water at 86° C. there was added 5% of the monomer emulsion and 20.3 g of 1.25% ammonium persulfate solution. After the initial charge had polymerized at 86° C., the remaining monomer emulsion and 28.7 g of 0.37% ammonium persulfate solution were gradually added over a period of one hour at 86° C. After completion of the monomer and initiator feed, the mixture was held at 86° C. for 15 minutes and then 10.0 g of 0.09% ammonium persulfate solution was added. After another 75 minutes at 86° C., the mixture was cooled and filtered. The filtrate was an approximately 30% solids emulsion copolymer dispersion in which the polymer composition is 10% monomer #6, 50% ethyl acrylate, and 40% methacrylic acid (polymer #L in Table II).

In the following Table II, there are listed several representative copolymers which constitute aqueous emulsion copolymer dispersion thickener compositions employed in the invention.

TABLE II

| | Polymer Monomers | Weight Ratio | % n-DLM | Viscosity[1], cps | |
|---|---|---|---|---|---|
| | | | | 1% | 3% |
| A | #1/EA/MAA | 10/50/40 | 0 | 4,600 | |
| B | #2/EA/MAA | 10/50/40 | 0 | 11,250 | |
| C | #2/EA/MAA | 2/58/40 | 0.2 | | 99 |
| D | #2/EA/MAA | 5/55/40 | 0.1 | 225 | |
| E | #3/EA/MAA | 10/50/40 | 0 | 19,150 | |
| F | #3/EA/MAA | 5/55/40 | 0 | 7,050 | |
| G | #3/EA/MAA | 2/58/40 | 0.2 | | 108 |
| H | #3/EA/MAA | 5/55/40 | 0.1 | 215 | |
| I | #4/EA/MAA | 10/50/40 | 0 | 41,000 | |
| J | #5/EA/MAA | 10/50/40 | 0 | 35,950 | |
| K | #5/EA/MAA | 5/55/40 | 0.3 | 65 | |
| L | #6/EA/MAA | 10/50/40 | 0 | >50,000 | |
| M | #6/EA/MAA | 5/55/40 | 0 | 33,750 | |
| N | #6/EA/MAA | 5/55/40 | 0.3 | 1,700 | |

Brookfield viscosity at 12 rpm for 1% and 60 rpm for 3% at 70° F., neutralized with one equivalent of NaOH.

EXAMPLE C

Surfactant Effect on Thickening Efficiency

The cothickening effect of added surfactant is shown in Table III. The data was obtained by blending in water the emulsion copolymer dispersion of polymer L of Example B above and the surfactant and then neutralizing with one equivalent of sodium hydroxide. Viscosities were measured at 75° F. using a Brookfield viscometer. The data illustrates a high level of viscosity enhancement and the viscosity dependence on the surfactant concentration.

TABLE III

Surfactant Cothickening (Polymer #L)[1]

| % Solid Surfactant[3] | Brookfield Viscosity[2], cps |
|---|---|
| 0 | 38,000 |
| 0.025 | 78,000 |
| 0.05 | 90,000 |
| 0.10 | 146,000 |
| 0.15 | 169,000 |
| 0.20 | 148,000 |
| 0.25 | 104,000 |
| 0.30 | 68,000 |
| 0.40 | 34,000 |
| 0.50 | 22,000 |

[1]Neutralized with one equivalent of NaOH at 0.5% polymer solids
[2]At 1.5 rpm
[3]Sodium lauryl sulfate

We claim:

1. A process of thickening an aqueous system, comprising adding to the system a water insoluble copolymer obtained by emulsion copolymerization of a monomer system comprising (1) about 0.5 to 30 weight percent of at least one di-ester of itaconic acid of the formula

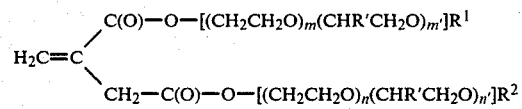

wherein
   $R^1$ and $R^2$, independently, are selected from the group consisting of alkyl, alkylaryl and polycyclic alkyl groups having 1 to 30 carbon atoms;
   m, m', n, n', independently are zero or a number having an average value of up to 60 or more, provided at least one of m and n is at least 2 and provided that the $R^1$ and $R^2$ group, when m or n, respectively, is at least 2, is one of said alkyl, alkylaryl and polycyclic alkyl groups having at least 8 carbon atoms;
   R' is $C_1$–$C_2$ alkyl; and
   the expressions $[(CH_2CH_2O)_m(CHR'CH_2O)_{m'}]R^1$ and $[(CH_2CH_2O)_n(CHR'CH_2O)_{n'}]R^2$ mean that the groups $(CH_2CH_2O)_m$ and $(CHR'CH_2O)_{m'}$ and the groups $(CH_2CH_2O)_n$ and $(CHR'CH_2O)_{n'}$, respectively, may be present in any random order or may be present in the exact order $(CH_2CH_2O)_m(CHR'CH_2O)_{m'}R^1$ or $(CH_2CHO)_n(CHR'CH_2O)_{n'}R^2$;

(2) about 10 to 70 weight percent of a copolymerizable ethylenically unsaturated monomer or monomer mixture selected from the group consisting of methyacrylic acid, acrylic acid, itaconic acid, acryloxypropionic acid, maleic acid, fumaric acid, citraconic acid and crotonic acid;

(3) at least 25 weight of at least one compound selected from the group consisting of compounds of the formula $H_2C=CYZ$ wherein
   (a) Y is H and Z is COOR", $C_6H_4R'''$, CN, Cl, OC(O)R"", $CONH_2$ or $CH=CH_2$;
   (b) Y is $C_1$–$C_4$ alkyl and Z is COOR", $C_6H_4R'''$, CN, $CONH_2$, or $CH=CH_2$; or
   (c) Y and Z are Cl; and
   R" is $C_1$–$C_8$ alkyl or $C_2$–$C_8$ hydroxyalkyl or lower alkoxy($C_2$–$C_8$)alkyl;
   R''' is H, Cl, Br or $C_1$–$C_4$ alkyl; and
   R"" is $C_1$–$C_8$ alkyl; and (4) zero to 1.0 weight percent of a polyethylenically unsaturated monomer.

2. The process of claim 1 wherein the polymer is an aqueous dispersion of a water-insoluble emulsion copolymer obtained by aqueous emulsion copolymerization of a monomer system comprising (1) about 10 to 70 weight percent of at least one member selected from the group consisting of methacrylic acid, acrylic acid, acryloxypropionic acid, and itaconic acid;

(2) about 0.5 to 25 weight percent of at least one monomer of the formula

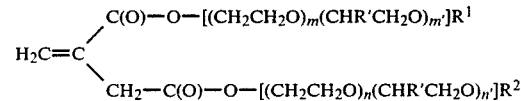

wherein
   $R^1$ and $R^2$, independently, are selected from the group consisting of alkyl, alkylaryl and polycyclic alkyl groups having 1 to 30 carbon atoms;
   m, m', n and n', independently, are zero or a number having an average value of up to 60 or more, provided that at least one of m and n is at least 2 and provided that the $R^1$ or $R^2$ group, when m or n, respectively, is at least 2, is one of said alkyl, alkylaryl and polycyclic alkyl groups having at least 8 carbon atoms;
   R' is $C_1$–$C_2$ alkyl; and
   the expressions $[(CH_1CH_2O)_m(CHR'CH_2O)_{m'}]R^1$ and $[(CH_2CH_2O)_n(CHR'CH_2O)_{n'}]R^2$ mean that the groups $(CH_2CH_2O)_m$ and $(CHR'CH_2O)_{m'}$ and the groups $(CH_2CH_2O)_n$ and $(CHR'CH_2O)_{n'}$, respectively, may be present in any random order or may be present in the exact order $(CH_2CH_2O)_m(CHR'CH_2O)_{m'}R^1$ or $(CH_2CH_2O)_n(CHR'CH_2O)_{n'}R^2$;

(3) at least 25 weight percent of at least one copolymerizable ethylenically unsaturated monomer selected from the group consisting of a compound of the formula $H_2C=CYZ$ wherein
   (a) Y is H and Z is COOR", $C_6H_4R'''$, CN, Cl, OC(O)R"", $CONH_2$, or $CH=CH_2$;
   (b) Y is $C_1$–$C_4$ alkyl and Z is COOR", $C_6H_4R'''$, $CONH_2$, or $CH=CH_2$; or (c) Y and Z are Cl; and
R'' is $C_1$-$C_8$ alkyl or $C_2$-$C_8$ hydroxyalkyl or lower alkoxy($C_2$-$C_8$)alkyl;
R''' is H, Cl, Br or $C_1$-$C_4$ alkyl; and
R'''' is $C_1$-$C_8$ alkyl; and
(4) zero to 1.0 weight percent of a polyethylenically unsaturated monomer;
the total of the percentages of monomers (1), (2), (3), and (4) being 100.

3. The process of claim 2 wherein the monomer system comprises
(1) about 10 to 70 weight percent of at least one member selected from the group consisting of methacrylic acid, acrylic acid, acryloxypropionic acid and itaconic acid;
(2) about 0.5 to 25 weight percent of at least one monomer of the formula

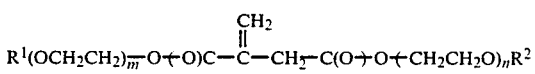

wherein
$R^1$ and $R^2$, independently, are selected from the group consisting of alkyl, alkyaryl and polycyclic alkyl groups having 1 to 30 carbon atoms; and
m and n, independently are zero or a number having an average value of up to 60 or more, provided that at least one of m and n is at least 2 and provided that at least one of the
$R^1$ or $R^2$ groups, when m or n, respectively, is at least 2, is one of said alkyl, alkylaryl, and polycyclic alkyl groups having at least 8 carbon atoms;
(3) at least 25 weight percent of at least one alkyl (meth)acrylate in which the alkyl group has 1 to 4 carbon atoms; and
(4) zero to 1.0 weight percent of a polyethylenically unsaturated monomer;
the total of the percentages of monomers (1), (2), (3) and (4) being 100.

4. A process according to claim 1, comprising adding to the system an aqueous dispersion of a water-insoluble emulsion copolymer obtained by aqueous emulsion copolymerization of a monomer system comprising
(1) about 10 to 70 weight of at least one of acrylic acid, methacrylic acid, and itaconic acid;
(2) about 0.5 to 25 weight percent of at least one di-ester of itaconic acid wherein at least one of a $C_8$-$C_{30}$ hydrocarbyl poly(oxyalkylene) group, the poly(oxyalkylene) moiety being at least two $C_2$-$C_4$ oxyalkylene groups; and
(3) at least 25 weight percent of at least one copolymerizable ethylenically unsaturated comonomer selected from $C_1$-$C_8$ alkyl, $C_2$-$C_8$ hydroxyalkyl and lower alkoxy($C_2$-$C_8$)alkyl acrylates, methacrylates and 1-alkenoates containing four to six carbons in the alkene-carbon chain; styrene and vinyl [($C_1$-$C_8$)alkyl]benzene, and [($C_1$-$C_8$)alkylphenoxy]alkenes containing three to six carbons in the alkene-carbon chain, acrylonitrile, methacrylonitrile, and cyanoalkenes containing four to six carbons in the alkene-carbon chain; vinyl and vinylidene chloride; vinyl esters of $C_2$-$C_9$ saturated aliphatic carboxylic acids; and polyethylenically unsaturated monomers and at least partially neutralizing said copolymer.

5. A process of thickening an aqueous system according to claim 4 wherein component (2) of the water-insoluble emulsion copolymer is a di-ester of itaconic acid wherein the two itaconic acid carboxy groups are each esterified by a $C_{12}$-$C_{18}$ hydrocarbyl poly(oxyethylene) group, the poly(oxyethylene) moiety being at least two oxyethylene groups.

6. A process of thickening an aqueous system according to claim 5 wherein component (3) of the water-insoluble emulsion copolymer is at least one of $C_1$-$C_4$ alkyl acrylates and methacrylates.

7. A process of thickening an aqueous system according to claim 6 wherein the water-insoluble emulsion copolymer is obtained by aqueous emulsion copolymerization of a monomer system consisting essentially of (1) about 30 to 45 weight percent of methacrylic acid; (2) about 1 to 15 weight of a di-ester of itaconic acid wherein the two itaconic acid carboxy groups are each esterified by a $C_{12}$-$C_{18}$ hydrocarbyl poly(oxyethylene) group, the average value of the number of oxyethylene groups in each poly(oxyethylene) chain being at least 10; and (3) about 40 to 60 weight percent of ethyl acrylate.

8. A process of thickening an aqueous system according to claim 4 wherein the water-insoluble emulsion copolymer is obtained by aqueous emulsion copolymerization of a monomer system consisting essentially of about 30 to 45 weight percent of component (1), and about 1 to 15 weight percent of component (2), and about 40 to 60 weight percent of component (3).

9. A process of thickening a water-based paint composition comprising adding an aqueous dispersion according to claim 1.

10. A process of thickening a water-based paint composition according to claim 9 wherein the paint composition comprises an aqueous dispersion of a vinyl addition emulsion polymer as a binder and pigment in a pigment volume concentration up to 65%.

11. A process of thickening an aqueous system according to claim 1 comprising adding an aqueous dispersion of a water-insoluble emulsion copolymer according to claim 1 and a surfactant, said surfactant being present in an amount effective to thicken the dispersion beyond the thickening provided by at least partial neutralization of said emulsion copolymer.

12. A method of thickening an aqueous system according to claim 11 wherein the surfactant is anionic or nonionic.

13. The process of thickening according to claim 1 a water-base paint comprising an aqueous dispersion of a vinyl addition emulsion polymer binder selected from vinyl acetate polymers, polymers of esters of acrylic acid, polymers of esters of methacrylic acid, styrene-butadiene polymers, copolymers of vinyl acetate and esters of acrylic acid, copolymers of vinyl acetate and esters of methacrylic acid, copolymers of vinyl acetate and esters of acrylic and methacrylic acid and copolymers of esters of acrylic and methacrylic acid, said paint containing a pigment having a PVC up to 65%, and containing at least partially neutralized emulsion copolymers according to claim 1 to control the rheological properties of the paint.

* * * * *